United States Patent
Elimelech et al.

(10) Patent No.: US 11,382,712 B2
(45) Date of Patent: Jul. 12, 2022

(54) MIRRORING IN IMAGE GUIDED SURGERY

(71) Applicant: Augmedics Ltd., Yokneam Illit (IL)

(72) Inventors: Nissan Elimelech, Beerotaim (IL); Stuart Wolf, Yokneam (IL); Nitzan Krasney, Haifa (IL)

(73) Assignee: AUGMEDICS LTD., Yokneam Illit (IL)

( * ) Notice: Subject to any disclaimer, the term of this patent is extended or adjusted under 35 U.S.C. 154(b) by 0 days.

(21) Appl. No.: 16/724,297

(22) Filed: Dec. 22, 2019

(65) Prior Publication Data
US 2021/0186647 A1    Jun. 24, 2021

(51) Int. Cl.
*A61B 90/00* (2016.01)
*G06T 11/00* (2006.01)
(Continued)

(52) U.S. Cl.
CPC ............ *A61B 90/37* (2016.02); *A61B 90/361* (2016.02); *G06T 7/73* (2017.01); *G06T 11/00* (2013.01);
(Continued)

(58) Field of Classification Search
CPC .................. A61B 90/37; A61B 90/361; A61B 2090/3937; A61B 2090/372;
(Continued)

(56) References Cited

U.S. PATENT DOCUMENTS 6,314,310 B1   11/2001   Ben-Haim et al.
7,107,091 B2   9/2006   Jutras et al.
(Continued)

FOREIGN PATENT DOCUMENTS

CA     3022448 A1   2/2018
CN    101379412 B   3/2009
(Continued)

OTHER PUBLICATIONS

Liao et al., "3-D Augmented Reality for MRI-Guided Surgery Using Integral Videography Autostereoscopic Image Overlay", IEEE Transactions on Biomedical Engineering, vol. 57, No. 6, pp. 1476-1486, 2010.
(Continued)

*Primary Examiner* — Sing-Wai Wu
*Assistant Examiner* — Khoa Vu
(74) *Attorney, Agent, or Firm* — Kligler & Associates Patent Attorneys Ltd

(57) ABSTRACT

An imaging system, including a head-mounted display worn by a system operator. A marker defines a plane when attached to a human subject. Optically reflective elements are disposed on the marker and on opposing sides of the plane in a non-symmetrical arrangement with respect to the plane. A memory stores a graphical representation of a tool used in a procedure performed on the human subject, and an image of anatomy of the human subject. A camera attached to the display acquires an image of the marker and the tool. A processor analyzes the image to identify the plane and to identify a side of the plane wherein the camera is located, and to render to the display the image of the anatomy of the human subject with the graphical representation of the tool superimposed thereon from a point of view in the identified side of the plane.

19 Claims, 9 Drawing Sheets

(51) Int. Cl.
  *G06T 7/73* (2017.01)
  *A61B 90/50* (2016.01)
(52) U.S. Cl.
  CPC ... *A61B 2090/372* (2016.02); *A61B 2090/373* (2016.02); *A61B 2090/3937* (2016.02); *A61B 2090/502* (2016.02); *G06T 2207/30204* (2013.01)
(58) Field of Classification Search
  CPC ........ A61B 2090/502; A61B 2090/373; G06T 7/73; G06T 11/00; G06T 2207/30204
  See application file for complete search history.

(56) References Cited

U.S. PATENT DOCUMENTS

| | | | |
|---|---|---|---|
| 7,556,428 | B2 | 7/2009 | Sukovic et al. |
| 7,630,753 | B2 | 12/2009 | Simon et al. |
| 7,768,702 | B2 | 8/2010 | Hirose et al. |
| 8,271,069 | B2 | 9/2012 | Jascob et al. |
| 8,306,305 | B2 | 11/2012 | Porat et al. |
| 8,690,776 | B2 | 4/2014 | Razzaque et al. |
| 8,848,977 | B2 | 9/2014 | Bammer et al. |
| 9,179,984 | B2 | 11/2015 | Teichman et al. |
| 9,220,573 | B2 | 12/2015 | Kendrick et al. |
| 9,269,192 | B2 | 2/2016 | Kobayashi |
| 9,378,558 | B2 | 6/2016 | Kajiwara et al. |
| 9,395,542 | B2 | 7/2016 | Tilleman et al. |
| 9,456,878 | B2 | 10/2016 | Macfarlane et al. |
| 9,495,585 | B2 | 11/2016 | Bicer et al. |
| 9,498,231 | B2 | 11/2016 | Haider et al. |
| 9,538,962 | B1 | 1/2017 | Hannaford et al. |
| 9,710,968 | B2 | 7/2017 | Dillavou et al. |
| 9,757,087 | B2 | 9/2017 | Simon et al. |
| 9,844,413 | B2 | 12/2017 | Daon et al. |
| 9,861,446 | B2 | 1/2018 | Lang |
| 9,872,733 | B2 | 1/2018 | Shoham et al. |
| 9,886,552 | B2 | 2/2018 | Dillavou et al. |
| 9,892,564 | B1 | 2/2018 | Cvetko et al. |
| 9,940,750 | B2 | 4/2018 | Dillavou et al. |
| 9,943,374 | B2 | 4/2018 | Merritt et al. |
| 9,959,629 | B2 | 5/2018 | Dillavou et al. |
| 10,010,379 | B1 | 7/2018 | Gibby et al. |
| 10,022,065 | B2 | 7/2018 | Ben-Yishai et al. |
| 10,022,104 | B2 | 7/2018 | Sell et al. |
| 10,034,713 | B2 | 7/2018 | Yang et al. |
| 10,080,616 | B2 | 9/2018 | Wilkinson et al. |
| 10,108,833 | B2 | 10/2018 | Hong et al. |
| 10,154,239 | B2 | 12/2018 | Casas |
| 10,166,079 | B2 | 1/2019 | McLachlin et al. |
| 10,181,361 | B2 | 1/2019 | Dillavou et al. |
| 10,194,131 | B2 | 1/2019 | Casas |
| 10,194,993 | B2 | 2/2019 | Roger et al. |
| 10,251,724 | B2 | 4/2019 | McLachlin et al. |
| 10,296,805 | B2 | 5/2019 | Yang et al. |
| 10,420,626 | B2 | 9/2019 | Tokuda et al. |
| 10,463,434 | B2 | 11/2019 | Siegler et al. |
| 10,499,997 | B2 | 12/2019 | Weinstein et al. |
| 10,504,231 | B2 | 12/2019 | Fiala |
| 10,537,395 | B2 | 1/2020 | Perez |
| 10,573,087 | B2 | 2/2020 | Gallop et al. |
| 10,586,400 | B2 | 3/2020 | Douglas |
| 10,792,110 | B2 | 10/2020 | Leung et al. |
| 10,799,316 | B2 | 10/2020 | Sela et al. |
| 10,838,206 | B2 | 11/2020 | Fortin-Deschenes et al. |
| 10,841,556 | B2 | 11/2020 | Casas |
| 10,842,461 | B2 | 11/2020 | Johnson et al. |
| 10,893,260 | B2 | 1/2021 | Trail et al. |
| 10,939,977 | B2 | 3/2021 | Messinger et al. |
| 11,058,390 | B1 | 7/2021 | Douglas |
| 2003/0210812 | A1 | 11/2003 | Khamene et al. |
| 2003/0225329 | A1 | 12/2003 | Rossner et al. |
| 2004/0030237 | A1 | 2/2004 | Lee et al. |
| 2005/0119639 | A1 | 6/2005 | McCombs et al. |
| 2006/0176242 | A1 | 8/2006 | Jaramaz et al. |
| 2008/0085033 | A1 | 4/2008 | Haven et al. |
| 2008/0183065 | A1 | 7/2008 | Goldbach |
| 2008/0221625 | A1 | 9/2008 | Hufner et al. |
| 2009/0018437 | A1 | 1/2009 | Cooke |
| 2010/0114110 | A1 | 5/2010 | Taft et al. |
| 2011/0004259 | A1 | 1/2011 | Stallings et al. |
| 2011/0098553 | A1 | 4/2011 | Robbins et al. |
| 2011/0105895 | A1 | 5/2011 | Kornblau et al. |
| 2011/0216060 | A1 | 9/2011 | Weising et al. |
| 2011/0254922 | A1 | 10/2011 | Schaerer et al. |
| 2012/0078236 | A1 | 3/2012 | Schoepp |
| 2012/0143050 | A1 | 6/2012 | Heigl |
| 2013/0106833 | A1 | 5/2013 | Fun |
| 2013/0237811 | A1* | 9/2013 | Mihailescu .......... A61B 90/361 600/424 |
| 2013/0278635 | A1 | 10/2013 | Maggiore |
| 2014/0114173 | A1 | 4/2014 | Bar-Tal et al. |
| 2014/0275760 | A1* | 9/2014 | Lee .................. G16H 40/63 600/102 |
| 2015/0005772 | A1 | 1/2015 | Anglin et al. |
| 2015/0150641 | A1 | 6/2015 | Daon et al. |
| 2015/0182293 | A1 | 7/2015 | Yang et al. |
| 2015/0209119 | A1 | 7/2015 | Theodore et al. |
| 2015/0351863 | A1 | 12/2015 | Plassky et al. |
| 2015/0366620 | A1 | 12/2015 | Cameron et al. |
| 2016/0125603 | A1* | 5/2016 | Tanji .................. A61B 17/152 382/131 |
| 2016/0324583 | A1 | 11/2016 | Kheradpr et al. |
| 2017/0027650 | A1 | 2/2017 | Merck et al. |
| 2017/0086941 | A1 | 3/2017 | Marti et al. |
| 2017/0112586 | A1* | 4/2017 | Dhupar ............. A61B 17/808 |
| 2017/0014119 | A1 | 6/2017 | Capote et al. |
| 2017/0164920 | A1 | 6/2017 | Lavallee et al. |
| 2017/0178375 | A1 | 6/2017 | Benishti et al. |
| 2017/0239015 | A1 | 8/2017 | Sela et al. |
| 2017/0251900 | A1 | 9/2017 | Hansen et al. |
| 2017/0252109 | A1 | 9/2017 | Yang et al. |
| 2017/0258526 | A1 | 9/2017 | Lang |
| 2017/0367771 | A1 | 12/2017 | Tako et al. |
| 2018/0018791 | A1* | 1/2018 | Guoyi ............... G02B 27/0176 |
| 2018/0028266 | A1 | 2/2018 | Barnes et al. |
| 2018/0036884 | A1 | 2/2018 | Chen et al. |
| 2018/0055579 | A1 | 3/2018 | Daon et al. |
| 2018/0092699 | A1 | 4/2018 | Finley |
| 2018/0133871 | A1 | 5/2018 | Farmer |
| 2018/0185100 | A1* | 7/2018 | Weinstein ............. A61B 34/20 |
| 2018/0200002 | A1 | 7/2018 | Kostrzewski et al. |
| 2018/0247128 | A1 | 8/2018 | Alvi et al. |
| 2018/0317803 | A1 | 11/2018 | Ben-Yishai et al. |
| 2019/0015163 | A1 | 1/2019 | Abhari et al. |
| 2019/0038362 | A1 | 2/2019 | Nash et al. |
| 2019/0046272 | A1 | 2/2019 | Zoabi et al. |
| 2019/0046276 | A1 | 2/2019 | Inglese et al. |
| 2019/0080515 | A1 | 3/2019 | Geri et al. |
| 2019/0105116 | A1 | 4/2019 | Johnson et al. |
| 2019/0175228 | A1 | 6/2019 | Elimelech et al. |
| 2019/0192230 | A1 | 6/2019 | Siemionow et al. |
| 2020/0085511 | A1 | 3/2020 | Oezbek et al. |
| 2020/0100847 | A1 | 4/2020 | Siegler et al. |
| 2020/0129136 | A1 | 4/2020 | Harding et al. |
| 2020/0129264 | A1 | 4/2020 | Onativia et al. |
| 2020/0138518 | A1* | 5/2020 | Lang .................... A61B 90/37 |
| 2020/0163723 | A1 | 5/2020 | Wolf et al. |
| 2020/0188034 | A1 | 6/2020 | Lequette et al. |
| 2020/0321099 | A1* | 10/2020 | Holladay ............. G06T 7/0012 |
| 2020/0337780 | A1 | 10/2020 | Winkler |
| 2020/0388075 | A1* | 12/2020 | Kazanzides ........... A61B 90/37 |
| 2021/0004956 | A1 | 1/2021 | Book et al. |
| 2021/0169504 | A1 | 6/2021 | Brown |
| 2021/0298835 | A1 | 9/2021 | Wang |

FOREIGN PATENT DOCUMENTS

| | | |
|---|---|---|
| CN | 111915696 A | 11/2020 |
| CN | 112489047 B | 3/2021 |
| EP | 3216416 A1 | 9/2017 |
| KR | 20140120155 A | 10/2014 |

(56) References Cited

FOREIGN PATENT DOCUMENTS

| WO | 2007051304 A1 | 5/2007 |
|----|---------------|--------|
| WO | 2018073452 A1 | 4/2018 |
| WO | 2019211741 A1 | 11/2019 |

OTHER PUBLICATIONS

International Application # PCT/IB2019/053524 search report dated Aug. 14, 2019.
U.S. Appl. No. 16/419,023 Office Action dated Sep. 3, 2020.
U.S. Appl. No. 16/199,281 Office Action dated Jun. 11, 2020.
Sagitov et al., "Comparing Fiducial Marker Systems in the Presence of Occlusion", International Conference on Mechanical, System and Control Engineering (ICMSC), pp. 1-6, 2017.
Liu et al., "Marker orientation in fiducial registration", Medical Imaging 2003: Image Processing, Proceedings of SPIE vol. 5032, pp. 1176-1185, 2003.
International Application # PCT/IB2020/056893 Search Report dated Nov. 9, 2020.
U.S. Appl. No. 16/200,144 Office Action dated Dec. 28, 2020.
International Application # PCT/IB2020/060017 Search Report dated Jan. 7, 2021.
U.S. Appl. No. 16/419,023 Office Action dated Jul. 22, 2021.
U.S. Appl. No. 16/200,144 Office Action dated Aug. 19, 2021.
International Application # PCT/IB2021/055242 Search Report dated Oct. 7, 2021.
JP Application # 2021525186 Office Action dated Dec. 1, 2021.
EP Application # 19796580.9 Search Report dated Dec. 20, 2021.
International Application # PCT/IB2021/058088 Search Report dated Dec. 20, 2021.
CN Application # 2019800757525 Office Action dated Mar. 1, 2022.
U.S. Appl. No. 16/200,144 Office Action dated Mar. 15, 2022.
U.S. Appl. No. 16/524,258 Office Action dated Apr. 11, 2022.
EP Application # 16767845.7 Office Action dated Apr. 29, 2022.
U.S. Appl. No. 16/419,023 Office Action dated Mar. 1, 2022.
Lorensen et al., "Marching Cubes: A High Resolution 3D Surface Construction Algorithm," ACM SIGGRAPH '87, Computer Graphics, vol. 21, No. 4, pp. 163-169, Jul. 1987.
Wikipedia, "Marching Cubes," pp. 1-4, last edited Sep. 4, 2021.
Milletari et al., "V-Net: fully Convolutional Neural Networks for Volumetric Medical Image Segmentation," arXiv:1606.04797v1, pp. 1-11, Jun. 15, 2016.

* cited by examiner

MIRRORING IN IMAGE GUIDED SURGERY

FIELD OF THE INVENTION

This invention relates generally to an augmented reality system, and specifically to correct image projection when it is used in image guided surgery.

BACKGROUND OF THE INVENTION

Correct imaging is important in image guided surgery, and a number of systems are known in the art for producing correct imaging.

U.S. Pat. Nos. 7,630,753 and 9,757,087, to Simon et al., describe a surgical instrument navigation system that allows a surgeon to invert the three-dimensional perspective of the instrument to match their perspective of the actual instrument.

U.S. Pat. No. 9,538,962, to Hannaford et al., describes a system for providing networked communications. The system includes a plurality of head-mountable devices, each in communication with a control system via a communication network.

U.S. Pat. No. 9,710,968, to Dillavou et al., describes a system for role designation with multiple sources.

U.S. Pat. No. 9,886,552, to Dillavou et al., describes a method for image registration that includes rendering a common field of interest that reflects a presence of a plurality of elements. At least one of the elements is a remote element located remotely from another of the elements.

U.S. Pat. No. 9,940,750, to Dillavou et al., describes a method for role negotiation that can comprise rendering a common field of interest that reflects a presence of a plurality of elements. At least one of the elements is a remote element located remotely from another of the elements.

U.S. Pat. No. 9,959,629, to Dillavou et al., describes a method for managing spatiotemporal uncertainty in image processing. The method can comprise determining motion from a first image to a second image.

U.S. Pat. No. 10,194,131, to Casas, describes a real-time surgery method for displaying a stereoscopic augmented view of a patient from a static or dynamic viewpoint of the surgeon. The method employs real-time three-dimensional surface reconstruction for preoperative and intraoperative image registration.

US Patent Application 2011/0216060, to Weising et al., describes a method for controlling a view of a virtual scene with a portable device. A signal is received and the portable device is synchronized to make the location of the portable device a reference point in a three-dimensional (3D) space.

US Patent Application 2017/0027650, to Merck et al., describes receiving data characterizing a mother video feed acquired by an endoscopic video capture device. The mother video feed can be for characterizing an operative field within a patient.

US Patent Application 2017/0251900, to Hansen et al., describes a depiction system for generating a real time correlated depiction of movements of a surgical tool for uses in minimally invasive surgery.

US Patent Application 2017/0367771, to Tako et al., describes a virtual reality surgical navigation method that includes a step of receiving data indicative of a surgeon's current head position, including a direction of view and angle of view of the surgeon.

US Patent Application 2018/0247128, to Alvi et al., describes a system for accessing a surgical dataset including surgical data collected during performance of a surgical procedure. The surgical data can include video data of the surgical procedure.

Documents incorporated by reference in the present patent application are to be considered an integral part of the application except that, to the extent that any terms are defined in these incorporated documents in a manner that conflicts with definitions made explicitly or implicitly in the present specification, only the definitions in the present specification should be considered.

SUMMARY OF THE INVENTION

An embodiment of the present invention provides an imaging system, consisting of:

a head-mounted display configured to be worn by an operator of the system;

a marker configured to be attached to a human subject and defining a plane when attached to the human subject, the marker having optically reflective elements disposed on the marker and on opposing sides of the plane in a non-symmetrical arrangement with respect to the plane;

a memory configured to store a graphical representation of a tool used in a procedure performed by the operator on the human subject, and an image of anatomy of the human subject;

a camera attached to the display and configured to acquire an input image of the marker and of the tool; and a processor configured to analyze the input image so as to identify the plane and to identify a side of the plane wherein the camera is located, and to render to the display the image of the anatomy of the human subject with the graphical representation of the tool superimposed thereon from a point of view in the identified side of the plane.

In a disclosed embodiment the plane makes an angle between +20° and −20° with a sagittal plane of the human subject. Alternatively, the plane makes an angle between +20° and −20° with an axial plane of the human subject.

In a further disclosed embodiment the marker has a two-dimensional surface which makes an angle between +20° and −20° with a frontal plane of the human subject.

In a yet further disclosed embodiment the marker defines a further plane and the optically reflective elements are disposed on opposing sides of the further plane in a non-symmetrical arrangement with respect to the further plane, and the processor is configured to analyze the input image so as to identify the further plane and to identify a side of the further plane wherein the camera is located, and to render to the display the image of the anatomy of the human subject with the graphical representation of the tool superimposed thereon from a point of view in the identified side of the further plane. Typically, the plane and the further plane are orthogonal to each other.

In an alternative embodiment the camera is located at a vertical height above the marker, and the processor is configured:

to ascertain the vertical height in response to the acquired input image of the marker;

to calculate a pair of planes, each of the pair having a preset acute angle to the identified plane and defining a first acute-angled wedge region and a second acute-angled wedge region to the identified plane; and when the display moves so that the point of view crosses the first acute-angled wedge region and the second acute-angled wedge region, or begins within the first acute-angled wedge region and crosses the second acute-angled wedge region, while the camera remains at the vertical height, to render to the display the image of the anatomy of the human subject with the graphical representation of the tool superimposed thereon from the point of view of a region opposite the identified side.

Typically the preset acute angle is less than or equal to 10°.

In a further alternative embodiment the camera is located at a vertical height above the marker, and the processor is configured:

to ascertain the vertical height in response to the acquired input image of the marker; and when the display moves so that the vertical height changes, to render unchanged to the display the image of the anatomy of the human subject with the graphical representation of the tool superimposed thereon.

There is further provided, according to an embodiment of the present invention, an imaging system, consisting of:

a first head-mounted display configured to be worn by a first operator of the system;

a second head-mounted display configured to be worn by a second operator of the system;

a marker configured to be attached to a human subject and defining a plane when attached to the human subject, the marker having optically reflective elements disposed on the marker and on opposing sides of the plane in a non-symmetrical arrangement with respect to the plane;

a memory configured to store a graphical representation of a tool used in a procedure performed by the first operator on the human subject, and an image of anatomy of the human subject;

a first camera attached to the first display and configured to acquire a first input image of the marker and of the tool;

a second camera attached to the second display and configured to acquire a second input image of the marker and of the tool; and a processor configured to:

analyze the first input image so as to identify the plane and to identify a first side of the plane wherein the first camera is located, and to render to the first display the image of the anatomy of the human subject with the graphical representation of the tool superimposed thereon from a first point of view in the identified first side of the plane, and analyze the second input image so as to identify the plane and to identify a second side of the plane wherein the second camera is located, and to render to the second display the image of the anatomy of the human subject with the graphical representation of the tool superimposed thereon from a second point of view in the identified second side of the plane.

There is further provided, according to an embodiment of the present invention, a method, consisting of:

providing a head-mounted display configured to be worn by an operator of an imaging system;

attaching a marker to a human subject, the marker defining a plane when attached, the marker having optically reflective elements disposed on the marker and on opposing sides of the plane in a non-symmetrical arrangement with respect to the plane;

storing in a memory a graphical representation of a tool used in a procedure performed by the operator on the human subject, and storing an image of anatomy of the human subject in the memory;

attaching a camera to the display;

acquiring an input image of the marker and of the tool with the camera; and analyzing the input image so as to identify the plane and to identify a side of the plane wherein the camera is located, and to render to the display the image of the anatomy of the human subject with the graphical representation of the tool superimposed thereon from a point of view in the identified side of the plane.

The present disclosure will be more fully understood from the following detailed description of the embodiments thereof, taken together with the drawings. A brief description of the drawings follows.

DETAILED DESCRIPTION OF EMBODIMENTS

Overview

Figure 1:
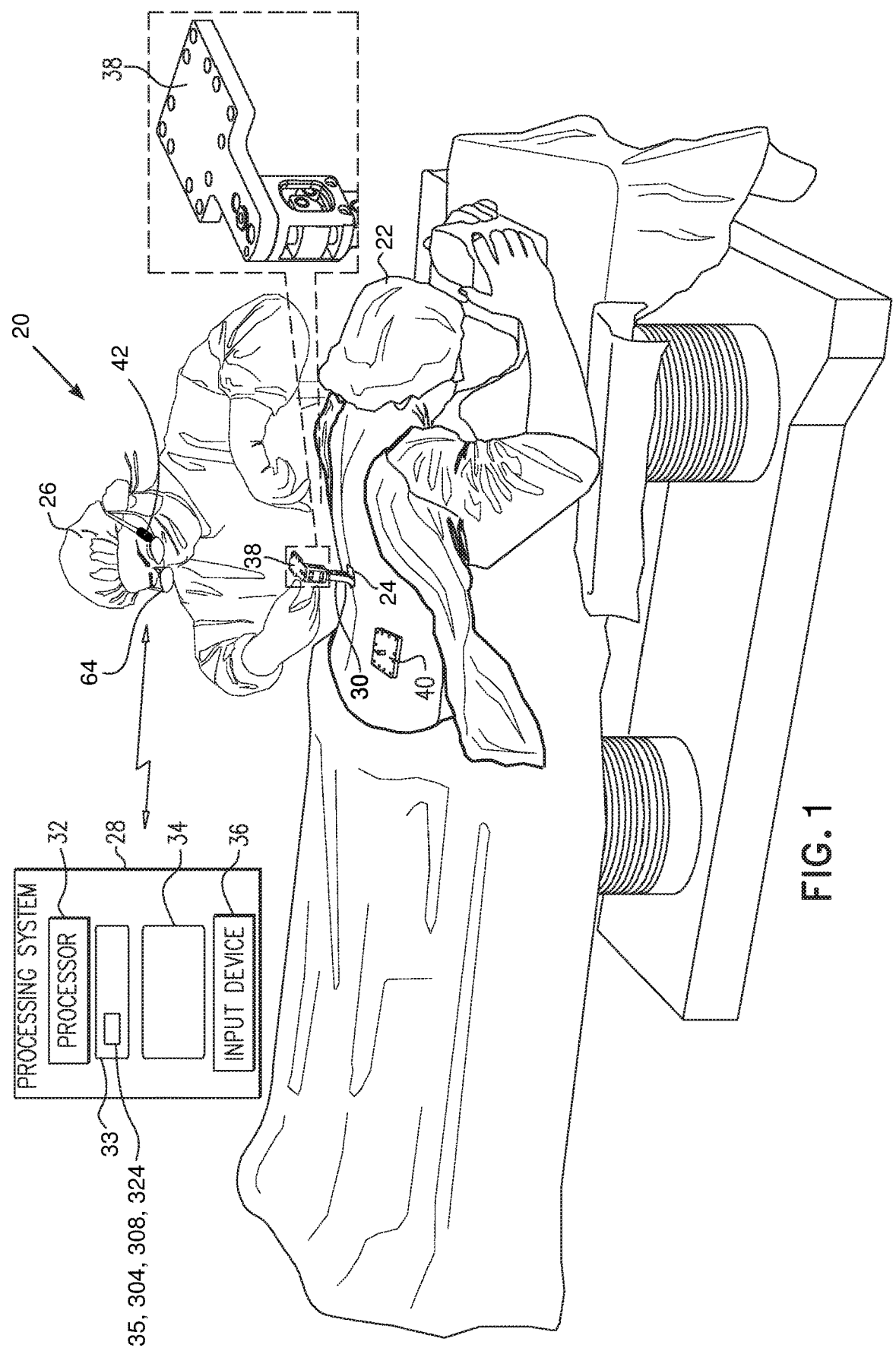
FIG. 1 is a schematic illustration of an initial preparatory stage of a medical procedure, according to an embodiment of the present invention.

A head-mounted display, for a medical procedure that implements an imaging system, such as an augmented reality system, in the display, typically needs to access stored computerized tomography (CT) files of the anatomy of a human subject. The display is worn by an operator of the system, and the accessed files are presented to the operator as scanned planes of the subject in the display. However, for the presentation to be correctly oriented, it is necessary to know the position of the operator with respect to the subject.

Embodiments of the present invention provide an imaging system that determines the operator position automatically, and so displays an image of the patient anatomy, and of a tool used in the procedure, automatically.

In addition to a head-mounted display (HMD) that is worn by an operator of the system, the system comprises a marker that is attached to the human subject. The marker defines a plane of asymmetry when attached to the human subject, since the marker has optically reflective elements disposed on the marker and on opposing sides of the plane in a non-symmetrical arrangement with respect to the plane. The plane of asymmetry is typically approximately parallel to one of the main anatomical planes of the human subject.

In the imaging system a memory stores a graphical representation of a tool used in the procedure performed by the operator, and the memory also stores an image of the anatomy of the human subject. A camera is attached to the HMD, and acquires an input image of the marker and of the tool. A processor analyzes the input image so as to identify the plane and to identify a side of the plane wherein the camera is located. The processor then renders to the display the image of the anatomy of the human subject with the graphical representation of the tool superimposed thereon from a point of view in the identified side of the plane.

Detailed Description

In the following, all directional references (e.g., upper, lower, upward, downward, left, right, top, bottom, above, below, vertical, and horizontal) are only used for identification purposes to aid the reader's understanding of the present invention, and do not create limitations, particularly as to the position, orientation, or use of embodiments of the invention.

In the description, like elements in the drawings are identified by like numerals, and like elements are differentiated as necessary by appending a letter to the identifying numeral.

Figure 3:
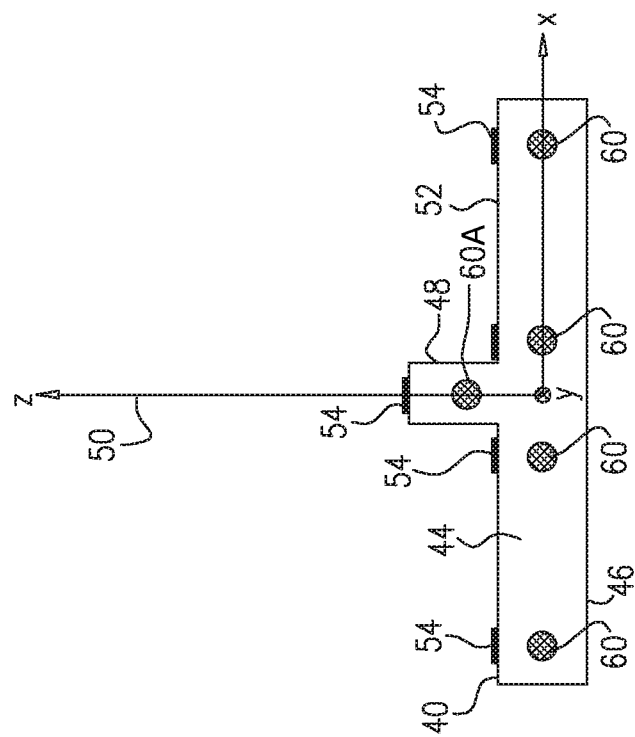
FIGS. 2, 3, and 4 are schematic depictions of entities used in the initial stage, according to an embodiment of the present invention.
Figure 2:
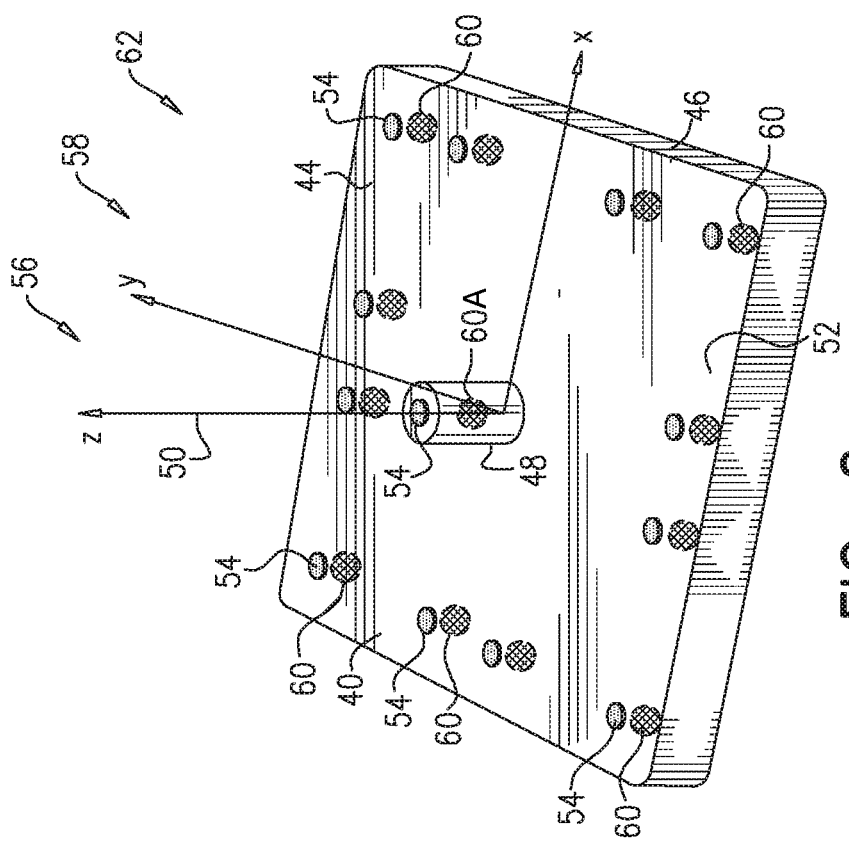
Figure 4:
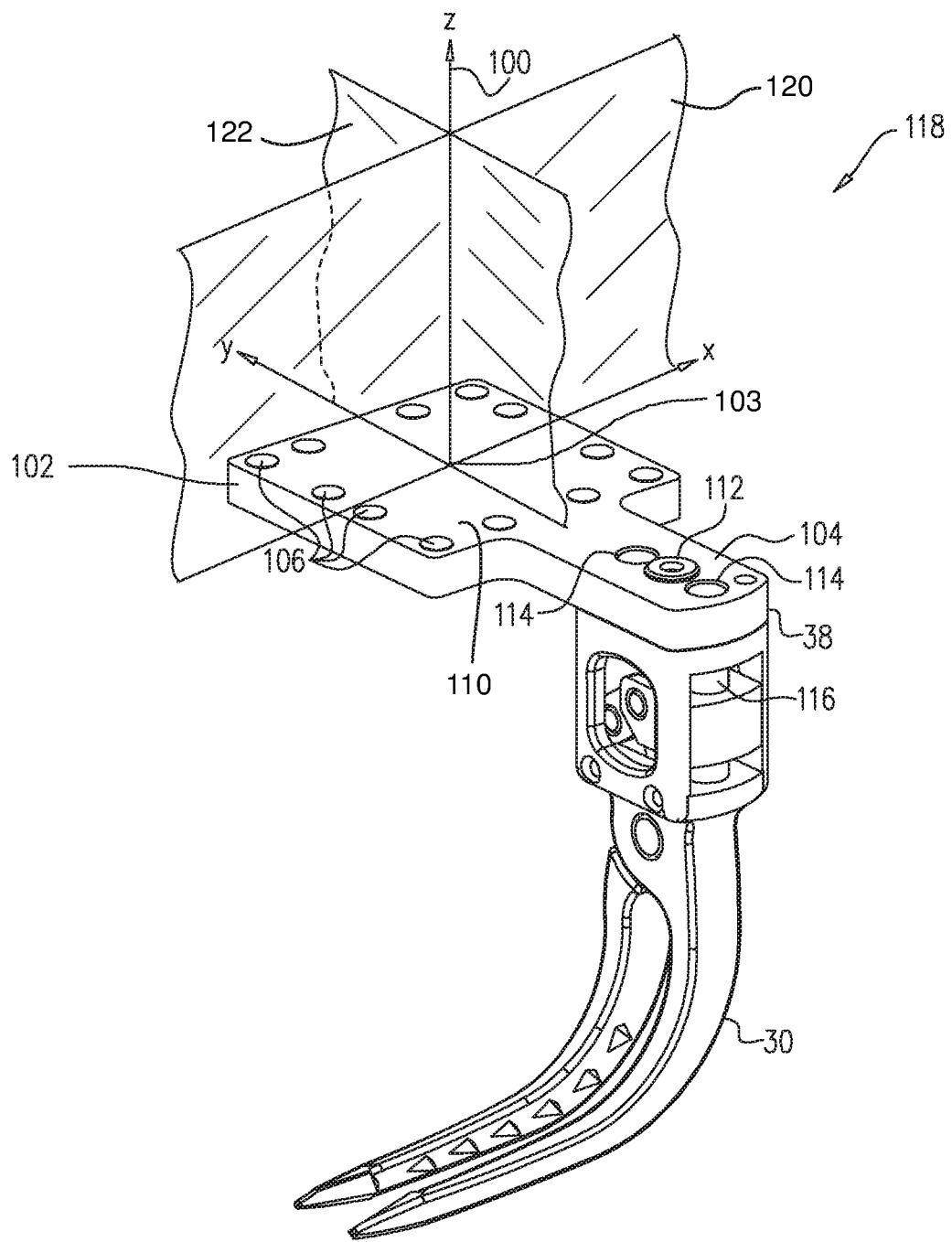

Reference is now made to FIGS. 1, 2, 3, and 4, which are diagrams according to an embodiment of the present invention. FIG. 1 is a schematic illustration of an initial preparatory stage of a medical procedure using an imaging system 20, and FIGS. 2, 3, and 4 are schematic depictions of entities used in the initial stage. The medical procedure exemplified here is performed on the back of a human subject 22, herein also termed patient 22, and during the initial stage of the procedure an operator 26 of system 20, also herein termed medical professional 26 makes an incision 24 into the patient's back. The professional inserts a spinous process clamp 30 into the incision, so that opposing jaws of the clamp are located on opposite sides of the spinous processes. The professional then slides the clamp over the vertebral laminas, and adjusts the clamp to grip one or more spinous processes, selected by the professional, of the patient. Clamp 30 is described below with reference to FIG. 4, and a clamp such as clamp 30 is described in more detail in U.S. Patent Application 2019/0175228 which is incorporated herein by reference.

Clamp 30 acts as a support for a patient marker 38, which is attached rigidly to the clamp. During substantially all of the procedure, i.e., during the initial, as well as the subsequent stages, patient marker 38 is used as a fiducial for patient 30, since because of its rigid connection to the patient, any movement of the patient is reflected in a corresponding motion of the patient marker. In order to operate as such a fiducial, in embodiments of the present invention, in the initial stage of the procedure marker 38 is registered with the anatomy of patient 30, herein assumed to comprise the skeleton of the patient, as is described herein.

During the procedure medical professional 26 wears a head-mounted display (HMD) 64 which is configured to present stored images, that are aligned with patient 22, to professional 26. HMD 64 is described further below.

As is also described below, in serving as a fiducial, marker 38 performs two functions: a first function wherein the marker is used to maintain registration between frames of reference of the head-mounted display and the patient's anatomy, and a second function wherein the marker is used to ascertain where the medical professional is located with respect to the patient. Thus, for the second function, the marker provides a location of the medical professional as being on a left side or a right side of the patient, or on an upper side or a lower side of the patient.

An augmented reality head-mounted display such as HMD 64 is described in more detail in U.S. Patent Application 2017/0178375 which is incorporated herein by reference.

During the initial stage of the procedure, a registration marker 40 is placed on the patient's back, and is used to implement the registration of patient marker 38 with the anatomy of patient 30. In contrast to patient marker 38, registration marker 40 is typically only used during the initial stage of the procedure, i.e., for the registration of the patient marker 38, and once the registration has been performed, for the subsequent procedure stages the registration marker may be removed from the patient's back. As will be apparent from the following description, only registration marker 40 is subject to fluoroscopy, and patient marker 38 is not subject to fluoroscopy.

Also during the initial stage of the procedure, a camera 42, fixedly attached to head-mounted display 64, is used to image the registration marker and the patient marker. Camera 42 typically operates in the visible and/or near-visible spectrum, i.e., at wavelengths of approximately 300 nm-900 nm.

A processing system 28 is coupled, by cables and/or wirelessly, to camera 42. System 28 comprises a computer processor 32, a memory 33 comprising stored images 35 that include images 304, 308, and 324, described below, a screen 34, and an input device 36 such as a pointing device. The system is configured to analyze the images acquired by the camera, as is described further below. Other functions of system 28 are also described below.

In order to operate, HMD 64 is coupled to processor of system 28, or alternatively HMD 64 has its own dedicated processor which performs similar functions to those performed by processor 32. When HMD 64 is operative it presents stored images, that are aligned with patient 22, to professional 26.

FIGS. 2 and 3 are respectively schematic perspective and cross-sectional views of registration marker 40, which is assumed to define a registration marker frame of reference 50, herein assumed to comprise an orthogonal set of xyz axes. Marker 40 is formed from a solid substrate 44, which is opaque to light in the visible and near-visible spectrum, and which is transparent to fluoroscopic radiation. Substrate 44 is typically formed from a hard plastic, such as polycarbonate, but any other solid material which is opaque to light and transparent to fluoroscopic radiation may be used in embodiments of the present invention.

In the illustrated embodiment of marker 40, substrate 44 is formed as a rectangular parallelepiped 46, upon which is mounted a pillar 48.

A plurality of optically reflective, but radiotransparent, discrete elements 54 are disposed on substrate 44. Elements 54 are hereinbelow, by way of example, assumed to comprise discs, and are also referred to herein as discs 54. It is understood that said optically reflective and radiotransparent elements may be of different shapes and/or sizes.

Some of the plurality of discs 54 are fixedly attached, typically by cementing, to a two-dimensional (2D) surface 52 of parallelepiped 46. These discs 54 are formed in a generally rectangular 2D pattern on surface 52. In addition, an optically reflective disc 54 is also cemented onto pillar 48, so that there is in totality a three-dimensional (3D) array of discs 54 disposed on the substrate. The 3D array of discs 54 are distributed on 2D surface 52, and on pillar 48, so that when marker 40 is illuminated and imaged by camera 50 the discs are easily distinguished from substrate 44. Furthermore, as explained in more detail below, the arrangement of discs 54 are configured to enable processor 32 to unambiguously determine the orientation and position of frame of reference 50 from the marker image.

The distributed discs 54 are herein assumed to comprise an optical component 56 of marker 40 that forms an optical pattern 58 for the marker. In a particular aspect of the invention optical pattern 58, comprising the distribution of discs 54, is implemented so that the pattern has no axis of symmetry and no plane of symmetry. The absence of both an axis and a plane of symmetry in the pattern ensures that the unambiguous determination of the orientation and position of the frame of reference of marker 40 is possible from the marker image for multiple different orientations and positions of the marker, the positions being typically within a region approximately 20 cm from the patient marker.

The description above of optical pattern 58 assumes that discs 54 are configured in three dimensions. However, as long as the pattern has no axis of symmetry and no plane of symmetry, the discs forming the pattern may be arranged in only two dimensions, for example, absent the disc on pillar 48. Thus, pattern 58 may be formed in at least two dimensions, i.e., in the case of discs 54, as a two-dimensional array of the discs or as a three-dimensional array of the discs.

It will be understood that the requirement for discs 54 to be arranged to form a pattern having an absence of both an axis and a plane of symmetry may be achieved using discs of substantially the same size and shape, wherein locations of the discs are selected so that the locations are arranged to have the absence of both an axis and a plane of symmetry. The described pattern is hereinbelow referred to as a unique optical pattern.

Alternatively, the unique optical pattern may be achieved using discs of different sizes and/or shapes. In this case, the locations of the discs may also satisfy the requirement, but this is not a necessity.

A multiplicity of radiopaque elements 60 are disposed in substrate 44 by being embedded in a distribution within parallelepiped 46. The distribution of elements 60 is arranged in a two dimensional radiopaque pattern 62 such that, as for the pattern of discs 54, the radiopaque pattern has no axis of symmetry and no plane of symmetry. Because substrate 44 is radiotransparent, and because of the absence of both an axis and a plane of symmetry in radiopaque pattern 62, a fluoroscopic, typically computerized tomography (CT), scan of the radiopaque elements of marker 40 enables the orientation and position of frame of reference 50 to be unambiguously determined by processor 32 from the fluoroscopic scan. In one embodiment elements 60 comprise spheres which are distributed in a 2D generally rectangular 2D pattern that is substantially the same as the rectangular pattern of discs 54 on surface 52.

The description above of elements 60 assumes that they are arranged in a radiopaque pattern of two dimensions. However, as long as the pattern has no axis of symmetry and no plane of symmetry, the elements forming the pattern may also be arranged in three dimensions, for example, by incorporation of a radiopaque element 60A, substantially similar to elements 60, in pillar 48. Thus, pattern 62 may also be formed in at least two dimensions, i.e., in the case of elements 60 and 60A, as a two-dimensional array of elements 60 or as a three-dimensional array of elements 60 and 60A.

As for discs 54, it will be understood that the requirement for elements 60 to be arranged to form a pattern having an absence of both an axis and a plane of symmetry may be achieved using elements of substantially the same size and shape, wherein locations of the elements are selected so that the locations are arranged to have the absence of both an axis and a plane of symmetry. The described pattern is hereinbelow referred to as a unique radiopaque pattern.

Alternatively, the unique radiopaque pattern may be achieved using elements of different sizes and/or shapes. In this case, the locations of the elements may also satisfy the requirement, but this is not a necessity.

The X-ray wavelengths of the CT scan are assumed to be in a range of 0.01-10 nm.

The above description of marker 40 assumes that discs 54 and elements 60 have different functionalities—the discs being optically reflective and radiotransparent, and the elements being radiopaque. In an alternative embodiment of marker 40 at least some of discs 54 are configured to have dual functionality by being optically reflective and radiopaque. As for the embodiment described above, in the alternative embodiment discs 54 are configured and distributed on substrate 44 so that an optical image of marker 40 provides an unambiguous determination of the orientation and position of frame of reference 50, and a fluoroscopic scan of the marker also provides an unambiguous determination of the orientation and position of the frame of reference.

The physical construction of the illustrated embodiment of marker 40, as a pillar attached to a rectangular parallelepiped, comprising an array of discs 54 and an array of elements 60, is but one example of possible physical constructions of the marker that enables an unambiguous determination of the marker's position and orientation from a camera image and from a fluoroscopic scan. In a disclosed embodiment, rather than marker 40 comprising pillar 48 mounted on substrate 44, an indentation (in place of the pillar) is formed within the substrate, and a disc 54 is located on a surface of the indentation.

Other suitable constructions for marker 40 are also considered to be within the scope of the present invention.

For example, the substrate of marker 40, rather than being formed from a parallelepiped with a pillar or an indentation, may be formed as substantially any conveniently shaped solid object that is opaque to light in the visible and near-visible spectrum and which is transparent to fluoroscopic radiation.

In addition, rather than the optical component of marker 40 being comprised of a plurality of discs 54 arranged in a particular pattern, the component may comprise any array or pattern of optical elements that is attached to the substrate, that is diffusely and/or specularly reflective, and that is configured to have the absence of axes and planes of symmetry described above, so that when imaged in visible or near-visible light an unambiguous determination of the marker's position and orientation may be made.

Referring to FIG. 4, patient marker 38 is assumed to define a patient marker frame of reference 100, assumed to comprise an orthogonal set of xyz axes. In the embodiment illustrated in FIG. 4 marker 38 comprises a rectangular parallelepiped substrate 102 to which is attached a tongue 104 used to fixedly connect the substrate to clamp 30. A center 103 of an upper surface of substrate 102 acts as an origin of the xyz axes.

The connection to clamp 30 is by a removable screw 112, and the patient marker connects in a predetermined fixed spatial relationship to the clamp using holes 114 which align with studs 116 of the clamp. Substrate 102 comprises a solid opaque material, and may be formed from any convenient material such as polyimide plastic.

A plurality of optically reflective discs 106, generally similar to discs 54, are attached, typically by cementing, to an upper 2D surface 110 of substrate 102. Discs 106, also referred to herein as reflectors 106, are formed in a generally rectangular 2D pattern on surface 110. Discs 106 are distributed so that when illuminated and imaged by camera 42 they are easily distinguished from substrate 102.

In addition, discs 106 are distributed with respect to an xz plane 120 and a yz plane 122 through origin 103. xz plane 120 and yz plane 122 are planes of asymmetry. Thus, discs 106 are arranged non-symmetrically with respect to xz plane 120, so that the distribution of the discs on one side of plane 120 do not mirror (through the plane) the discs on the opposing side of the plane. In addition, discs 106 are arranged non-symmetrically with respect to yz plane 122, so that the distribution of the discs on one side of plane 122 do not mirror the discs on the opposing side of the plane.

In FIG. 4 discs 106 are shown as being distributed on sides of a rectangle, however, it will be understood that this is but one example for the positioning of the discs on surface 110. Other distributions of discs 106, providing that they define planes of asymmetry as described above, are also assumed to be comprised within the scope of the present invention.

Furthermore, it will be appreciated that the physical construction of patient marker 38 described above is by way of example. Thus, embodiments of the present invention comprise any patient marker formed of any conveniently shaped solid opaque substrate to which is attached an optical pattern, the pattern defining planes of asymmetry as described above.

Figure 5:
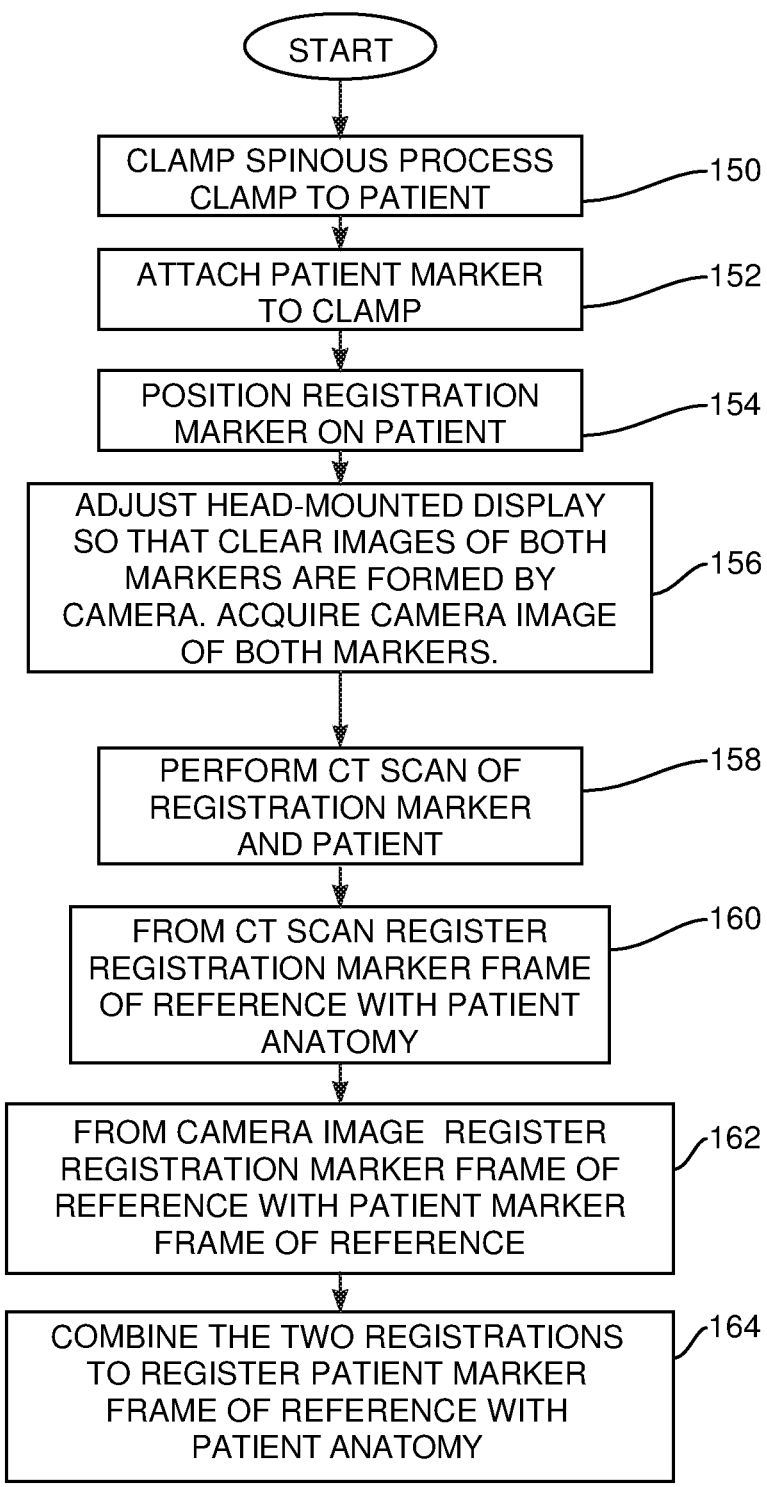
FIG. 5 is a flowchart of steps performed to register a patient marker with the anatomy of a patient during the initial preparatory stage.

FIG. 5 is a flowchart of steps performed to register patient marker 38 with the anatomy of patient 22 during the initial preparatory stage of a medical procedure illustrated in FIG. 1, according to an embodiment of the present invention. While the following description assumes, for simplicity, a CT scan, other types of fluoroscopic imaging are also considered to be within the scope of the present invention.

In an initial step 150, medical professional 26 makes an incision in the back of patient 22, inserts spinous clamp 30 into the patient, and then clamps the clamp to one or more of the processes of the patient.

In a patient marker step 152, the medical professional attaches patient marker 38 to spinous clamp 30, ensuring that the marker is rigidly attached to the clamp. Marker is attached to clamp 30 so that surface 110, corresponding to the xy plane of the xyz axes, is approximately parallel to a frontal plane of patient 22, xz plane of asymmetry 120 is approximately parallel to a sagittal plane of the patient, and so that yz plane of asymmetry 122 is approximately parallel to an axial plane of the patient. As used herein, the term "approximately parallel" as applied to two planes indicates that the planes subtend an angle within a range of ±20° to each other.

In a registration marker step 154, the professional places registration marker 40 on the skin of the back of the patient, typically as close to the patient's spine as is convenient.

In a camera step 156, professional 26 adjusts his/her position so that camera 42, attached to head-mounted display 64 images the registration marker and the patient marker. Professional 26 adjusts their position so that the images formed by camera 42 of the registration marker and of the patient marker are clear images, i.e., that neither marker occludes the other. Typically processor 32 of processing system 28 is configured to verify the acceptability of the two marker images, and if necessary the professional may use and communicate with system 28 to adjust, in an iterative manner, their position and/or that of the registration marker until system 28 provides an indication to the professional that acceptable images are being generated.

Once acceptable images are being generated, a camera image of the two markers is acquired, and is provided to processing system 28.

In a fluoroscopic scan step 158, a CT scan of patient 22, in the vicinity of marker 40 is performed, and processing system 28 acquires the scan. The scan may be performed by inserting patient 22 into a CT scanning system so that marker 40 is scanned. The insertion may be implemented by bringing the CT scanning system to patient 22, or by transporting the patient to the system. In either case, marker 40 remains in the marker's position of step 156.

In a scan analysis step 160, processor 32 analysis the CT scan acquired in step 158, the scan comprising an image of radiopaque elements 60 and of the anatomy of patient 22. From the acquired image, processor 32 calculates the position and orientation of registration marker frame of reference 50, and registers the frame of reference with the anatomy of the patient. The registration typically comprises a set of vectors P between selected points on registration marker 40 and selected vertebrae of patient 22. In one embodiment, the registration comprises using a 4×4 homogenous transformation, comprising a 3×3 rotation and a 1×3 translation, that transforms a point in the space of patient 22 to a point in registration marker frame of reference 50.

In a camera image analysis step 162, processor 32 analyzes the camera image of patient marker 38 and registration marker 40 acquired in step 156. From the acquired image, processor 32 calculates the position and orientation of registration marker frame of reference 50, and the position and orientation of patient marker frame of reference 100. Once the processor has calculated the positions and orientations of the two frames of reference, it formulates a registration of the two frames of reference as a set of vectors Q describing the transformation of the registration marker frame of reference to the patient marker frame of reference.

In a concluding analysis step 164, the processor adds the two sets of vectors found in steps 160 and 162 to formulate a registration set of vectors R between the patient marker frame of reference 36 and the patient anatomy, as shown in equation (1):

$$R=P+Q \qquad (1)$$

Figure 6:
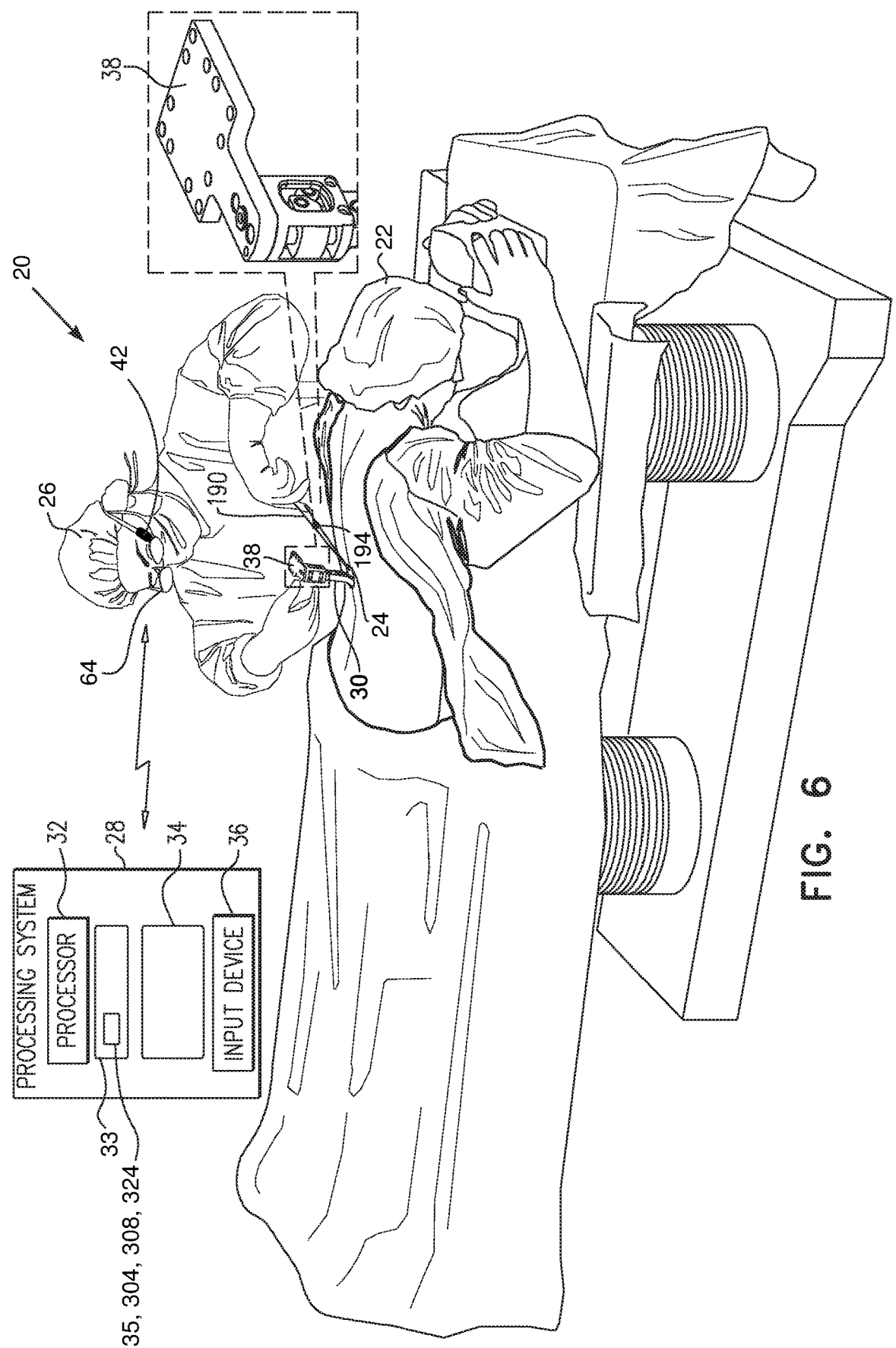
FIG. 6 is a schematic illustration of a subsequent stage of the procedure, according to an embodiment of the present invention.
Figure 7:
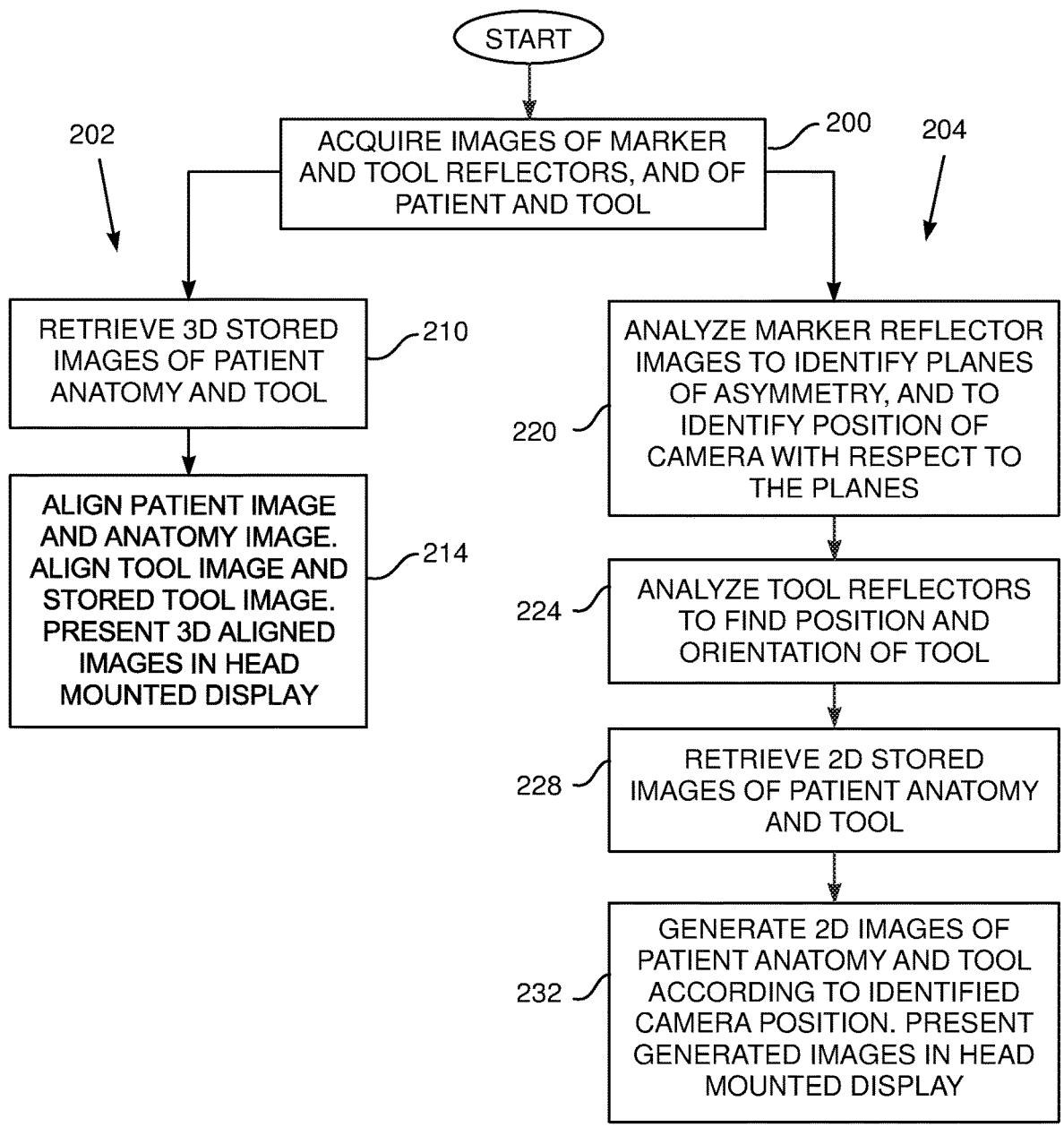
FIG. 7 is a flowchart of steps performed during the subsequent stage, according to an embodiment of the present invention.
Figure 8:
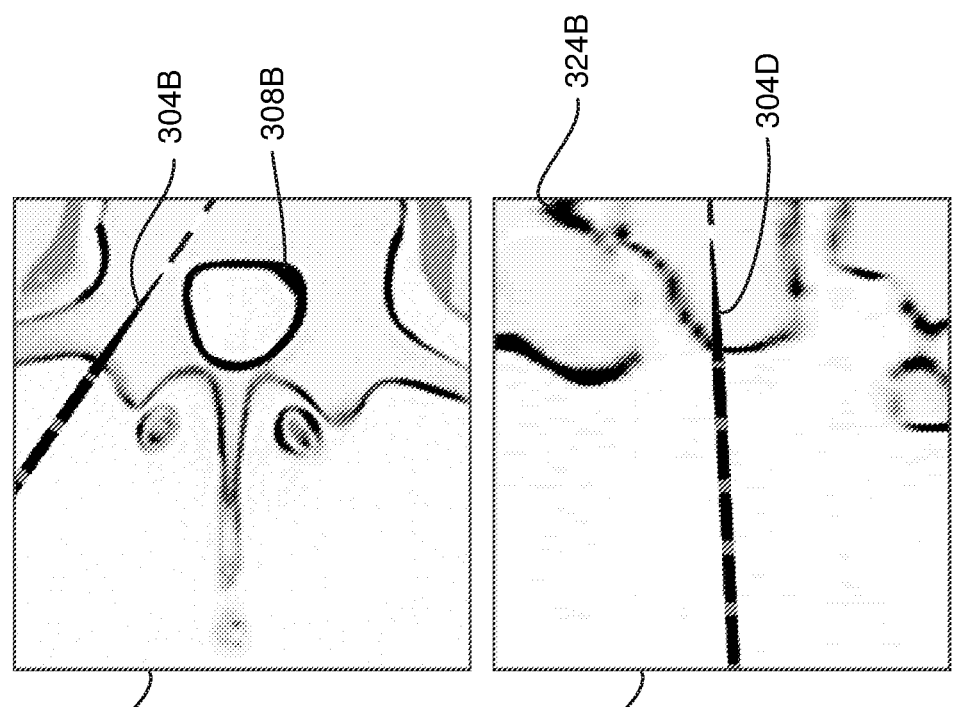
FIG. 8 shows schematic figures illustrating images generated in the subsequent stage, according to an embodiment of the present invention.
Figure 8:
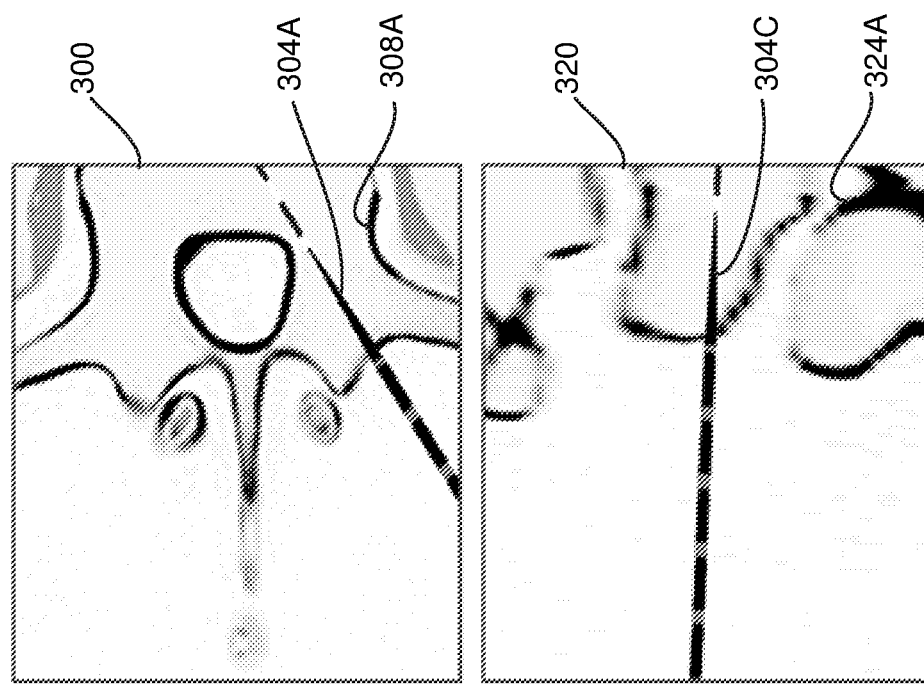

FIG. 6 illustrates a subsequent stage of the medical procedure, FIG. 7 is a flowchart of steps performed during the subsequent stage, and FIG. 8 shows schematic figures illustrating images generated in the subsequent stage, according to an embodiment of the present invention. In the subsequent stage registration marker 40 has been removed from the back of patient 22, and medical professional 26 operates on the patient using a surgical tool 190. The tool is tracked by the HMD processor, by having identifying reflectors 194, generally similar to reflectors 106, attached to the tool.

In an initial step 200 of the flowchart of FIG. 7, the HMD projects visible or invisible light to patient marker 38 and tool 190. Camera 42 acquires images of reflectors 106 of the marker, of reflectors 194 of tool 190 and of patient 22 and tool 190.

The flowchart then branches into two paths, a first path 202 and a second path 204. Processor 32 implements steps of both paths substantially simultaneously.

In first path 202, in a three-dimensional (3D) image retrieval step 210, processor 32 retrieves a 3D stored patient anatomy image of patient 22, typically comprising a CT image of the patient, from stored images 35. The processor also retrieves a stored virtual image, also herein termed a stored representation, of tool 190 from the stored images.

In a 3D image presentation step 214, the processor presents aligned 3D images of the patient anatomy and of the virtual tool image in the head mounted display.

The position of the virtual tool image is determined from reflectors 194. In order to ensure that the anatomy image and the virtual tool image, projected by the display, align with the anatomy of patient 22 and with the actual tool image, the processor determines the position and orientation of frame of reference 100 of the patient marker from the acquired images of reflectors 106. The processor applies the registration set of vectors R, found in step 164 of the flowchart of FIG. 5, to the position and orientation of the marker frame of reference, so as to effect the alignment.

In second path 204, in a plane identification step 220, processor 32 analyzes the images of reflectors 106 acquired by camera 42 to identify the position and orientation of xz plane of asymmetry 120 and yz plane of asymmetry 122. From the images the processor also calculates and stores the height of camera 42 above the xy plane.

From the identified positions and orientations of the planes the processor determines on which side of the planes camera 42 resides. Each plane has two sides, and it will be understood that the two planes divide the volume around marker 38 into four regions, the camera residing in one of four regions.

In a tool reflector step 224 the processor analyzes the images of reflectors 194 to find the position and orientation of tool 190.

In an image retrieval step 228 the processor retrieves a stored virtual image of the tool. The processor also retrieves, from the stored 2D images, images of the patient anatomy at the tool position, and parallel to the axial and sagittal planes of the patient.

In an image presentation step 232, the processor uses the retrieved images to generate a combined image of the patient anatomy with a representation of the tool superimposed on the patient anatomy, from a point of view of the camera, i.e., from a point of view in the plane sides identified in step 220.

The processor presents the combined image in HMD 64 for viewing by professional 26.

By presenting images in HMD 64 according to the point of view of camera 42, embodiments of the present invention present correctly oriented images to operator 26, who is wearing the HMD. It will also be understood that the correct orientation is determined according to the position of the operator 26 with respect to the patient, i.e., whether the operator is to the left or right of the patient, and whether the operator is on a lower or upper side of the patient.

FIG. 8 shows schematic illustrations of images generated in step 232, according to an embodiment of the present invention.

A diagram 300 illustrates an image 304A of tool 190 superimposed on an image 308A of the patient anatomy, from a point of view in a left side of a sagittal plane of patient 22, and a diagram 312 illustrates an image 304B of tool 190 superimposed on an image 308B of the patient anatomy, from a point of view in a right side of the patient sagittal plane. The two diagrams are mirror images of each other, and use a stored image 304 of tool 190. The two diagrams also use a stored image 308 of the patient anatomy that is parallel to the patient sagittal plane at an identified position of tool 190.

A diagram 320 illustrates an image 304C of tool 190 superimposed on an image 324A of the patient anatomy, from a point of view in a lower side of an axial plane of patient 22, and a diagram 330 illustrates an image 304D of tool 190 superimposed on an image 324B of the patient anatomy, from a point of view in an upper side of the patient axial plane. As for diagrams 300, 312, the two diagrams 320, 330 are mirror images of each other, and use stored image 304 of tool 190. Diagrams 320, 330 use a stored image 324 of the patient anatomy that is parallel to the patient axial plane at the identified position of tool 190.

Returning to the flowchart of FIG. 7, it will be appreciated that professional 26 may select which images, referred to in steps 214 and 232, are rendered for viewing in the head-mounted display. Thus the professional may view either the 3D images of step 214, or the 2D images of step 232, or both images simultaneously.

Figure 9:
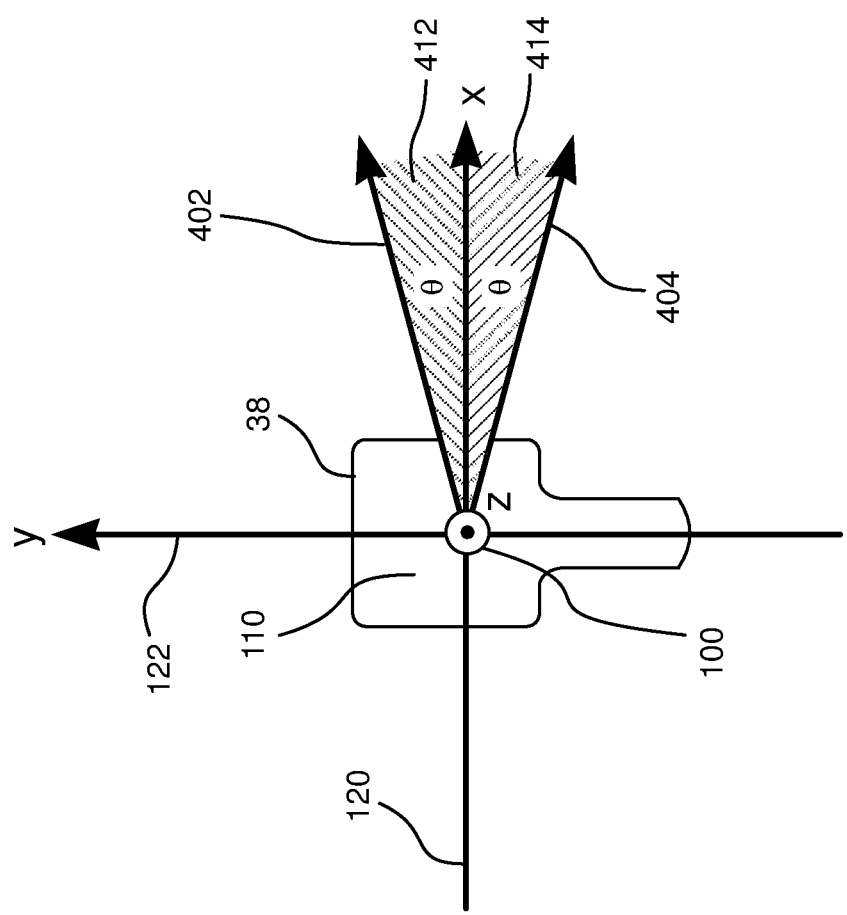
FIG. 9 is a schematic top-down view of a surface of a marker used in the procedure.

FIG. 9 is a schematic top-down view of surface 110 of marker 38, showing the x, y, and z axes of the marker, as well as xz plane 120 and yz plane 122.

As operator 26 moves from one side of xz plane 120 to the other side, then following on from step 232 of the flowchart of FIG. 7 together with the diagrams of FIG. 8, the images presented to the operator are mirror images of each other. The mirroring is also true when the operator moves from one side of yz plane 122 to the other side.

A disclosed embodiment of the present invention places a limitation on the mirroring described above when moving from one side of a plane to another, in order to reduce jitter in the presented images when the operator is close to the plane. In order to reduce jitter, the processor constructs transition regions around xz plane 120 and other transition regions around yz plane 122. The following description is for the transition region around xz plane 120 and to the right of yz plane 122.

Processor 32 constructs a first plane 402 containing and terminating at the z axis, and at an angle $+\theta$ from xz plane 120, and a second plane 404 containing and terminating at the z axis, and at $-\theta$ from xz plane 120. In one embodiment $\theta \leq 10°$. The two planes form respective wedge-shaped regions 412, 414 with xz plane 120, and these two wedge-shaped regions comprise the transition region around xz plane 120 and to the right of yz plane 122.

If the movement across xz plane 120 includes both wedge-shaped regions being crossed, by the HMD and the attached camera of the operator, or begins from within one of the wedge-shaped regions and crosses the other one, then the mirroring as described above is implemented.

However, if the movement across the xz plane does not comply with the movements above, e.g., the movement only crosses one wedge-shaped region and stops in the other region, or only moves between wedge-shaped regions, then no mirroring is implemented.

For a transition region around xz plane 120 and to the left of yz plane 122, the processor constructs two planes making angles $\pm\theta$ with the xz plane, generally similar to planes 402 and 404, so as to form two more wedge-shaped regions terminating at the z axis and to the left of the yz plane.

The processor constructs the same type of transition regions for yz plane 122. Thus, for a transition region around yz plane 122 and above xz plane 120, the processor constructs two planes making angles $\pm\theta$ with the yz plane, generally similar to planes 402 and 404, so as to form two wedge-shaped regions terminating at the z axis and above the xz plane.

Similarly, for a transition region around yz plane 122 and below the xz plane, the processor constructs two planes making angles $\pm\theta$ with the yz plane, generally similar to planes 402 and 404, so as to form two wedge-shaped regions terminating at the z axis and below the xz plane.

There are thus a total of four transition regions distributed symmetrically about the z-axis, each transition region comprising two wedge-shaped regions.

As for the movement for the illustrated transition region, if movement across either of planes 120 or 122 includes both wedge-shaped regions being crossed, by the HMD and the attached camera of the operator, or begins from within one of the wedge-shaped regions and crosses the other one, then the mirroring is implemented.

However, if the movement across either of the planes does not comply with the movements above, then no mirroring is implemented, i.e., mirroring is precluded.

Another disclosed embodiment of the present invention places another limitation on the mirroring described above. In this embodiment, when the operator moves to look over patient 22, mirroring is also precluded. To preclude mirroring for this embodiment, the processor checks if the camera height, measured in step 220 of the flowchart of FIG. 7 has changed, as is the case if operator 26 moves her/his head to look over patient 22. I.e., if the camera height changes, no mirroring is implemented regardless of whether the xz plane or the yz plane have been crossed.

Figure 10:
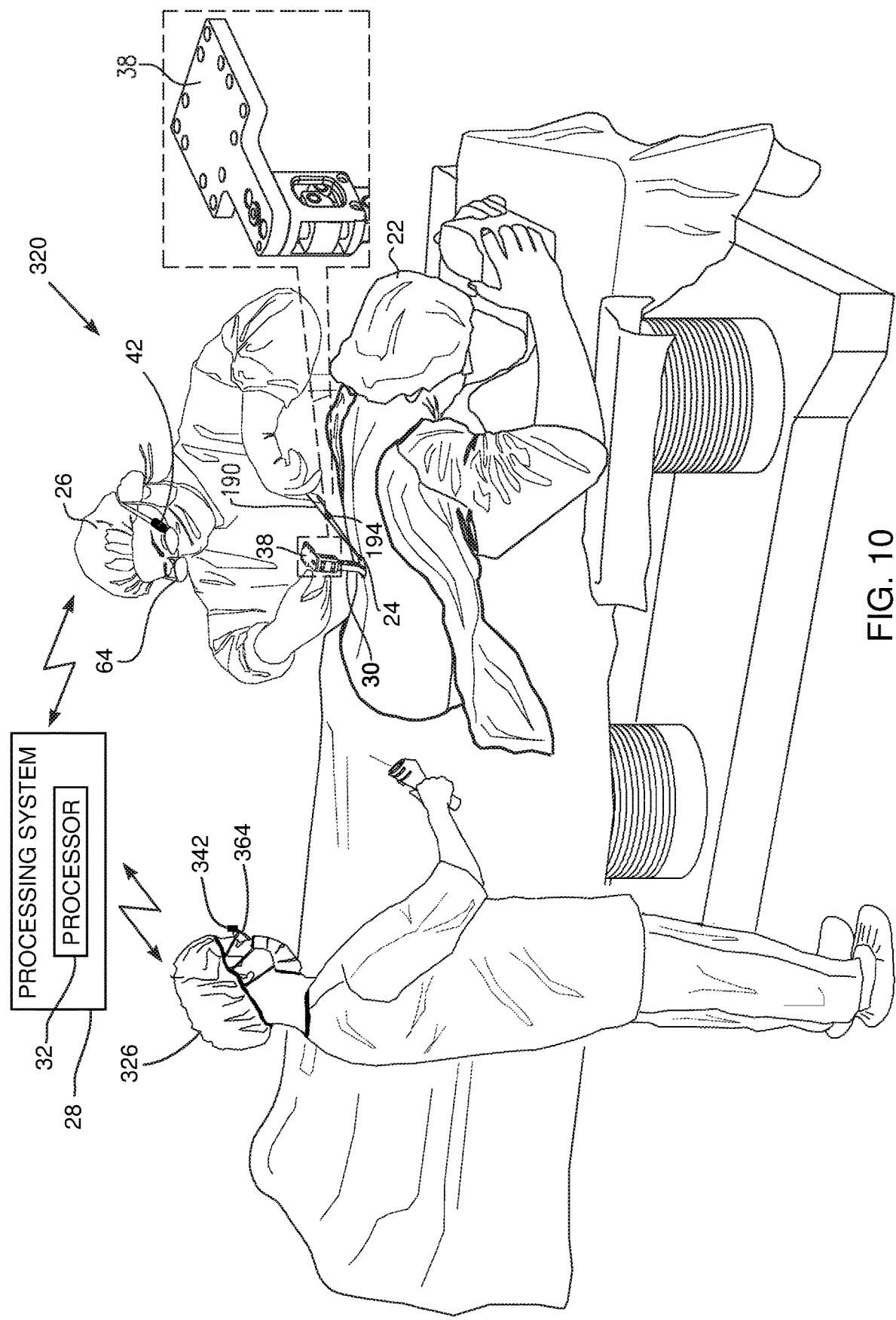
FIG. 10 is a schematic illustration of the subsequent stage of the procedure when there are two operators for the procedure, according to an embodiment of the present invention.

FIG. 10 is a schematic illustration of the subsequent stage of the procedure, when two operators use an imaging system 320, according to an embodiment of the present invention. Apart from the differences described below, the operation of system 320 is generally similar to that of system 20 (FIGS. 1-9), and elements indicated by the same reference numerals in both systems 20 and 320 are generally similar in construction and in function.

In contrast to system 20, system 320 is used by operator 26 and a second operator 326. Second operator 326 wears an HMD 364, and a camera 342 is fixedly attached to the HMD. HMD 364 and camera 342 are respectively substantially similar in construction and function to HMD 64 and camera 42. However, camera 342 is typically not used to perform the registration described in the flowchart of FIG. 5, since this is provided by camera 42.

Images generated in HMD 364 are substantially as described in the flowchart of FIG. 7. Thus, images presented in HMD 364 are oriented according to the point of view of camera 342, i.e., according to whether operator 326 is to the left or right of patient 22, and according to whether the operator is on the lower or upper side of the patient.

It will be understood that by presenting images in a head-mounted display according to the point of view of the camera attached to the display, embodiments of the present invention present correctly oriented images to a wearer of the head-mounted display. It will also be understood that the correct orientation is determined according to the position of the wearer of the HMD with respect to the patient, i.e., whether the wearer is to the left or right of the patient, and whether the wearer is on a lower or upper side of the patient.

It will be further understood that for cases where there is more than one HMD, each being worn by a respective wearer, embodiments of the present invention operate simultaneously and independently to present correctly oriented images to each wearer, according to the position of the respective wearer with respect to the patient. A wearer on the right side of the patient and a wearer on the left side of the patient are presented with mirror images based on anatomy images parallel to the patient sagittal plane; similarly a wearer on the lower side of the patient and a wearer on the upper side of the patient are presented with mirror images based on anatomy images parallel to the patient axial plane.

It will thus be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. An imaging system, comprising:
a head-mounted display configured to be worn by an operator of the system;
a patient marker configured to be attached to a human subject;
optically reflective elements disposed on the patient marker so as to define at least one plane of asymmetry thereon, by being disposed on opposing sides of the at least one plane of asymmetry in a non-symmetrical arrangement with respect to the at least one plane of asymmetry, so that the elements on a first side of the at least one plane of asymmetry do not mirror, through the at least one plane of asymmetry, the elements on a second, opposing, side of the at least one plane of asymmetry;
a memory configured to store a graphical representation of a tool used in a procedure performed by the operator on the human subject, and an image of anatomy of the human subject;
a camera attached to the head-mounted display and configured to acquire an input image of the patient marker including the optically reflective elements, and of the tool including identifying tool-reflectors attached thereto, while the operator operates on the human subject using the tool; and
a processor configured to:
analyze the input image of the patient marker and the tool, so as to identify whether the camera is located to a right side or to a left side of the human subject, or whether the camera is located on a first side or on a second, opposing, side of an axial plane of the human subject; and
render to the head-mounted display the image of the anatomy of the human subject with the graphical representation of the tool superimposed thereon from a point of view in the identified side of the human subject.

2. The imaging system according to claim 1, wherein the at least one plane of asymmetry makes an angle between +20° and −20° with a sagittal or the axial plane of the human subject.

3. The imaging system according to claim 1, wherein the patient marker comprises a two-dimensional surface which makes an angle between +20° and −20° with a frontal plane of the human subject.

4. The imaging system according to claim 1, wherein the camera is located at a vertical height above the patient marker, and the processor is configured:
to ascertain the vertical height in response to the acquired input image of the patient marker;
to calculate a pair of planes, each of the pair having a preset acute angle one of a sagittal plane or the axial plane of the human subject and defining a first acute-angled wedge region and a second acute-angled wedge region to the one of the planes; and
when the display moves so that the point of view crosses the first acute-angled wedge region and the second acute-angled wedge region, or begins within the first acute-angled wedge region and crosses the second acute-angled wedge region, while the camera remains at the vertical height, to render to the display the image of the anatomy of the human subject with the graphical representation of the tool superimposed thereon from the point of view of a region opposite the identified side of the human subject.

5. The imaging system according to claim 4, wherein the preset acute angle is less than or equal to 10°.

6. The imaging system according to claim 1, wherein the camera is located at a vertical height above the patient marker, and the processor is configured:
   to ascertain the vertical height in response to the acquired input image of the patient marker; and
   when the head-mounted display moves so that the vertical height changes, to render unchanged to the head-mounted display the image of the anatomy of the human subject with the graphical representation of the tool superimposed thereon.

7. The imaging system according to claim 1, further comprising:
   an additional head-mounted display configured to be worn by an additional operator of the system;
   an additional camera attached to the additional head-mounted display and configured to acquire an additional input image of the patient marker and the tool,
   wherein the processor is further configured to:
   analyze the additional input image of the patient marker, and the tool, so as to identify whether the additional camera is located to the right side or to the left side of the human subject, or whether the camera is located on the first side or on the second, opposing, side of the axial plane of the human subject; and
   render to the additional head-mounted display the image of the anatomy of the human subject with the graphical representation of the tool superimposed thereon from an additional point of view in the identified side of the human subject.

8. The system according to claim 7, wherein when the operator is located to the right side of the human subject and the additional operator is located to the left side of the human subject, or when the operator is located on the first side of the axial plane of the human subject and the additional operator is located on the second side of the axial plane of the human subject the rendering to the additional display of the image of the anatomy of the human subject with the graphical representation of the tool superimposed thereon, is mirrored.

9. The system according to claim 1, wherein the processor is further configured to track the patient marker and the tool.

10. The system according to claim 1, wherein when the operator moves from one side of the human subject to an opposing side, wherein the sides are selected from: the right side and the left side of the human subject, or the first side of the axial plane of the human subject and the second side of the axial plane of the human subject, the rendering to the head-mounted display comprises mirroring of the image of the anatomy of the human subject with the graphical representation of the tool superimposed thereon.

11. The imaging system according to claim 1, wherein the identified side is determined in response to formulating a registration set of vectors between a patient marker frame of reference and the anatomy of the human subject.

12. A computerized method, the method comprising:
    storing in a memory a graphical representation of a tool used in a procedure performed by an operator of an imaging system on a human subject, and an image of anatomy of the human subject;
    accessing an input image of a patient marker attached to the human subject and of the tool including identifying tool-reflectors attached thereto, wherein the image is acquired by a camera attached to a head-mounted display configured to be worn by the operator while the operator operates on the human subject using the tool, the patient marker comprising optically reflective elements disposed on the patient marker so as to define at least one plane of asymmetry thereon, by being disposed on opposing sides of the at least one plane of asymmetry in a non-symmetrical arrangement with respect to the at least one plane of asymmetry, so that the elements on a first side of the at least one plane of asymmetry do not mirror, through the at least one plane of asymmetry, the elements on a second, opposing, side of the at least one plane of asymmetry; and
    analyzing the input image of the patient marker and the tool, so as to identify whether the camera is located to a right side or to a left side of the human subject, or whether the camera is located on a first side or on a second, opposing, side of an axial plane of the human subject; and
    rendering to the head-mounted display the image of the anatomy of the human subject with the graphical representation of the tool superimposed thereon from a point of view in the identified side of the human subject.

13. The method according to claim 12, wherein the at least one plane of asymmetry makes an angle between +20° and −20° with a sagittal or the axial plane of the human subject.

14. The method according to claim 12, wherein the camera is located at a vertical height above the patient marker, the method further comprising:
    ascertaining the vertical height in response to the acquired input image of the patient marker;
    calculating a pair of planes, each of the pair having a preset acute angle to one of a sagittal plane or the axial plane of the human subject and defining a first acute-angled wedge region and a second acute-angled wedge region to the one of the planes; and
    when the display moves so that the point of view crosses the first acute-angled wedge region and the second acute-angled wedge region, or begins within the first acute-angled wedge region and crosses the second acute-angled wedge region, while the camera remains at the vertical height, rendering to the display the image of the anatomy of the human subject with the graphical representation of the tool superimposed thereon from the point of view of a region opposite the identified side of the human subject.

15. The method according to claim 12, wherein the camera is located at a vertical height above the patient marker, the method further comprising:
    ascertaining the vertical height in response to the acquired input image of the patient marker; and
    when the display moves so that the vertical height changes, rendering unchanged to the head-mounted display the image of the anatomy of the human subject with the graphical representation of the tool superimposed thereon.

16. The method according to claim 12, further comprising determining the location and orientation of the patient marker and tracking the tool based on the input image.

17. The method according to claim 12, wherein when the operator moves from one side of the human subject to an opposing side, wherein the sides are selected from: the right side and the left side of the human subject, or the first side of the axial plane of the human subject and the second side of the axial plane of the human subject, the rendering to the display comprises mirroring of the image of the anatomy of the human subject with the graphical representation of the tool superimposed thereon.

18. An imaging system, comprising:
a head-mounted display configured to be worn by an operator of the system;
a memory configured to store a graphical representation of a tool used in a procedure performed by the operator on the human subject, and an image of anatomy of the human subject;
a camera attached to the head-mounted display and configured to acquire an input image of a patient marker and of the tool, subsequent to an initial stage of registration of the patient marker with the anatomy of the human subject, wherein the patient marker is attached to the human subject;
optically reflective elements disposed on the patient marker so as to define at least one plane of asymmetry thereon, by being disposed on opposing sides of the at least one plane of asymmetry in a non-symmetrical arrangement with respect to the at least one plane of asymmetry, so that the elements on a first side of the at least one plane of asymmetry do not mirror, through the at least one plane of asymmetry, the elements on a second, opposing, side of the at least one plane of asymmetry; and
a processor configured to:
analyze the input image of the patient marker, and of the tool so as to identify whether the camera is located to a right side or to a left side of the human subject, or whether the camera is located on a first side or on a second, opposing, side of an axial plane of the human subject; and
render to the head-mounted display the image of the anatomy of the human subject with the graphical representation of the tool superimposed thereon from a point of view in the identified side of the human subject.

19. The system according to claim 18, wherein the processor is further configured to align the rendering to the head-mounted display of the image of the anatomy of the human subject with the graphical representation of the tool superimposed thereon with the anatomy of the human subject based on the registration.

* * * * *